US00PP11099P

United States Patent [19]

Moore

[11] Patent Number: Plant 11,099

[45] Date of Patent: Oct. 19, 1999

[54] MINIATURE ROSE PLANT NAMED 'MORSHODOT'

[76] Inventor: Ralph S. Moore, 2519 E. Noble Ave., Visalia, Calif. 93292

[21] Appl. No.: 09/004,842

[22] Filed: Jan. 9, 1998

[51] Int. Cl.[6] ..... A01N 5/00

[52] U.S. Cl. ..... Plt./122

[58] Field of Search ..... Plt./122, 129

[56] References Cited

U.S. PATENT DOCUMENTS

P.P. 7,375 11/1990 Jacobs ..... Plt./116

P.P. 7,384 11/1990 Meilland ..... Plt./122

P.P. 8,193 4/1993 Moore ..... Plt./122

P.P. 8,242 6/1993 Meilland ..... Plt./122

*Primary Examiner*—Howard J. Locker

[57] ABSTRACT

This invention relates to a new and distinct cultivar of minature rose, primarily identified by the deep red color of its petals and double flowers.

1 Drawing Sheet

The present invention relates to a new and distinct cultivar of hardy, dwarf, bush type rose plant of the miniature class. The cultivar being primarily characterized — as to novelty by its deep red color and double flowers.

The cultivar is further characterized by:

An abundance of bloom, with flowers ususally borne several to the stem.

No Fragrance.

A plant of vigorous, rounded to upright growth shape, with semi-glossy foliage with broad pointed leaflets; the buds and flowers being similar in form to 'MORfire' ('Ring of Fire',miniature rose; U.S. Plant Pat. No. 6,618) but differing in color, being deep red instead of yellow blend.

A plant which grows and blooms satisfactorily both in greenhouse and outdoors; with repeat bloom, is good for growing in pots, and provides excellent garden decoration as well as cut flowers.

The present cultivar of miniature rose was originated by me at my nursery, located at Visalia, Calif., under conditions of careful control and observation, as a result of a cross between 'FOUtell' U.S. Plant Pat. No. 7,375) ('Show N', Tell, miniature rose) as the seed parent and 'MORdort' ('Sincerely Yours') as the pollen parent.

Subsequent to my origination of the cultivar I successfully asexually reproduced this new cultivar at my nursery, located as aforementioned, by budding as well as by cuttings; the reproductions have run the true in all respects. The photograph illustrates the cultivar including the foliage, buds and flowers (Top, side and reverse).

Plant part coloration illustrated is as true as reasonably possible to attain in photographic illustrations of this type.

Referring now specifically to the new and distinct cultivar of miniature rose plant, the following is a detailed description thereof in outline; all major color plant identification being by reference to *The R.H.S.Colour Chart* (Royal Horticultural Society) except where common terms of color definition are employed.

As compared to cultivar 'MORgal' ('Galaxy', miniature rose; U.S. Plant Pat. No. 4,680): The present cultivar is of more spread out habit, has larger, more double flowers and holds the red color better.

Type: Hardy; dwarf; spreading; seedling; greenhouse; outdoors; cut flowers; garden decoration; potted plant.

Class: Miniature. Cultivar identification: 'MORshodot' (commercial synonym: Cherry HI).

Flowers borne; Usually in small clusters, on sturdy, wiry stems.

Quantity of bloom: Abundant both outside and inside greenhouse.

Bud;

*Peduncle.*—Medium length; slender but sturdy; erect; medium green, near Green Group 138B, sometimes tinted bronze (outdoors); nearly smooth.

*Before calyx breaks.*—Size — small.

*Form.*—Pointed, with several small foliaceous appendages on surface of the bud; with foliaceous parts extending beyond the tip of the bud equal to one half or more than one half of its length.

*Color.*—Medium green, near Green Group 138B, occasionally tinted with bronze (outdoors). As calyx breaks — Color — red, near Red Group 53A or darker. Opening — Opens well in all weather.

Bloom;

*Size when fully open.*—Small, averaging about 40mm or 1¾" .

*Petalage.*—Double — averaging 50 or more petals, arranged regularly plus several small petaloids.

*Form.*—Full, high centered at first, becoming rounded with petals rolled loosely outward and downward. Fully opened flowers may show stamens (not shown in photo).

*Sepals.*—Permanent; spear shaped; recurved.

*Behavior.*—Opens well in all weather; spent petals of flowers drop off.

*Flower longevity* (*August* 1997).—Plant in pot — 4 to 6 days or longer. Cut flowers at living room temperature — 4 to 5 days.

Petals; Fairly thick; satiny on inside and on outside surface.

*Shape.*—Outside petals: broad lanceolate (wedge shaped) with small acute tip. Intermediate: broad lanceolate with nearly round or short acute tip. Inside: lanceolate with acute tip.

*Color.*—(Newly opening flower from plant grown in plastic greenhouse in October, 1997, Visalia, Calif. (Photograph taken October 1997)). Outside petal: Outside surface — red near Red Group 53A (may be darker at times) with small white area at petal base. Inside surface — near Red Group 53A with small white area at petal base. Intermediate petal: Outside surface similar to outside petal. Inside surface similar to to outside petal. Inner petal: Outside surface similar to intermediate petal. Inside surface similar to intermediate petal. General color effect: newly opened flowers — dark red (velvety) 3 days open — color similar to newly opened flower. Flower (petal) color holds well as flowers age.

Reproductive organs:

*Stamens.*—Moderately abundant, arranged regulary about the pistil.

*Filaments.*—Fairly short, white to yellowish.

*Anthers.*—Well formed, yellow.

*Pollen.*—Moderate.

*Pistils.*—Average number.

*Styles.*—Long; whitish; bunched.

*Ovaries.*—All enclosed in calyx.

*Hips.*—Some, round, orange.

*Seed.*—Some (few).

Foliage:

*Leaves.*—Compound of five (sometimes 3 or 7) leaflets; medium small); leathery; semi-glossy.

*Leaflets.*—Shape: Broad lanceolate; apex acute; base — rounded. Color: Medium to dark green (can be as dark as Green 137A); new growth — normal (medium) green sometimes tinted reddish. Rachis: Medium strenth; upper side smooth; grooved; underside smooth or may have several small thorns (or claws). Stipules: Medium to short length; medium width; medium to short length narrow points which turn out usually at about 45° or less. Color similar to leaflets.

*Habit.*—Dwarf; bush; spreading; much branched. Plant height: 35–40cm. Plant spread: 35–40cm.

*Growth.*—Vigorous; internodes short.

*Canes.*—Medium slender; sturdy.

*Main stems.*—Color: Medium green, near Green Group 139B.

*Thorns.*—Average, slender, long, usually straight to slightly downward, color: brown to gray. Hairs — few or none.

The miniature rose plant and its flowers as heretofore described may vary in slight detail due to climate, soil and cultural cinditions under which the cultivar may be grown; the present descripton being of the cultivar as grown at Visalia, Calif.

The following is claimed.

1. A new and distinct cultivar of rose plant of the miniature class, of hardy, dwarf. bushy, much branched habit substantially as illustrated and described, characterized by buds and flowers, basically dark red, the bud being short and pointed in the early stage, resembling in form 'MORfire' (miniature), with the open flower being double and rounded with 40–50 or more petals; and further characterized by a plant of compact, vigorous, spreading shape with main stems and shoots of average thorniness, the said plant being easy to propagate from soft-wood cuttings with an abundance of small, semi-glossly foliage, the flowers being usually borne in small clusters on medium length stems.

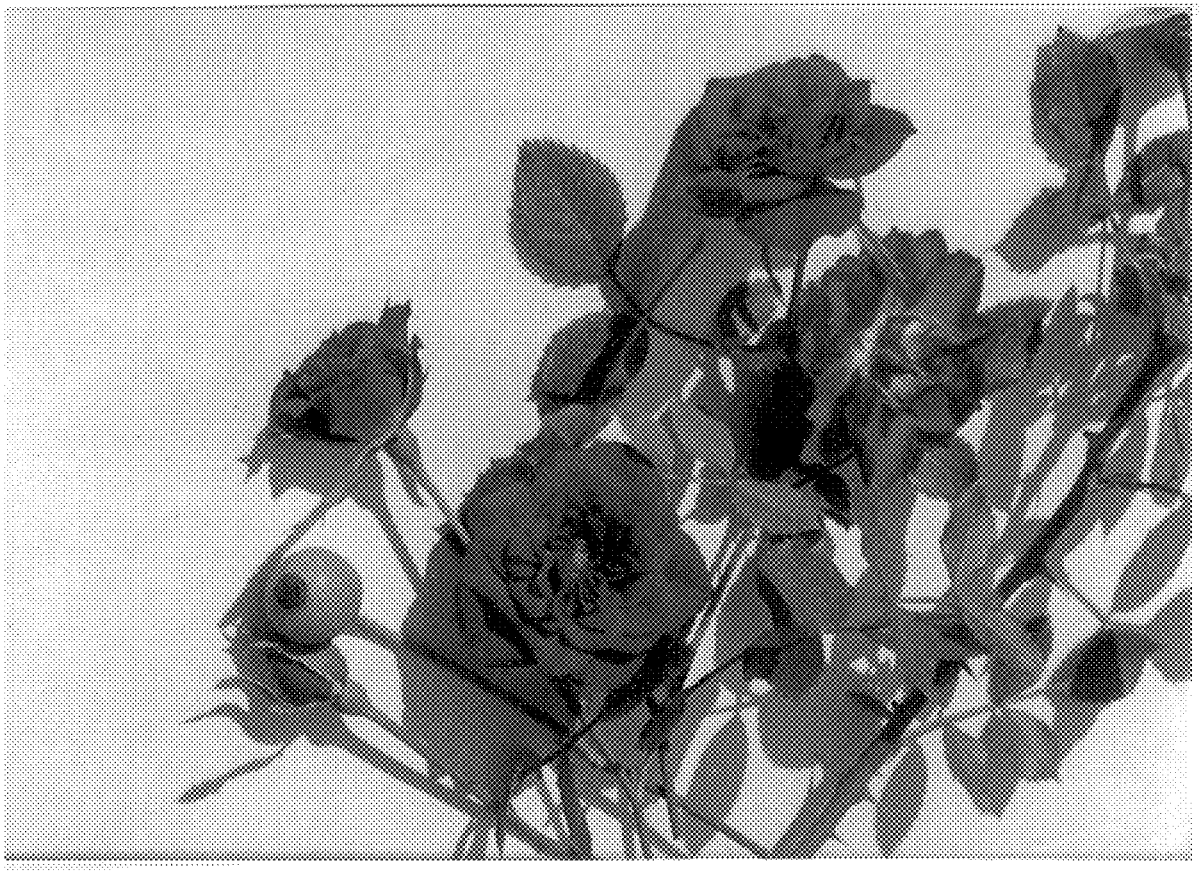

* * * * *